United States Patent [19]

Chen et al.

[11] Patent Number: 5,497,781
[45] Date of Patent: Mar. 12, 1996

[54] RECORDING BIOLOGICAL SIGNALS USING HILBERT TRANSFORMS

[76] Inventors: Yunquan Chen, 1000-2725 Melfa Road, Vancouver, British Columbia, V6T 1N4; Charles A. Laszlo, 4750 Belmont Road, Vancouver, British Columbia, V6T 1A9; Cecil Hershler, 6370 Alma Street, Vancouver, British Columbia, V6N 1Y6, all of Canada

[21] Appl. No.: 208,407

[22] Filed: Mar. 10, 1994

Related U.S. Application Data

[63] Continuation-in-part of Ser. No. 969,458, Oct. 30, 1992, Pat. No. 5,299,572, and a continuation-in-part of Ser. No. 156,732, Nov. 24, 1993, Pat. No. 5,443,559.

[51] Int. Cl.$^6$ ................................................ A61B 5/0488
[52] U.S. Cl. ............................................................. 128/733
[58] Field of Search ..................................... 128/733, 731, 128/639, 642

[56] References Cited

U.S. PATENT DOCUMENTS

5,047,930   9/1991   Martens et al. ........................ 128/731

FOREIGN PATENT DOCUMENTS

538739        4/1993   European Pat. Off. .
WO88110093  12/1988   WIPO .

OTHER PUBLICATIONS

Basano et al., "Real–Time FFT . . . ", IEEE Trans. Biomed Eng, vol. BME–33, No. 11, Nov. 1986, pp. 1049–1051.
M. Knaflitz, IEEE Micro, vol. 11, no. 5, Oct. 1991, New York, U.S.A. pp. 12–15 and 48–56.
M. M. Figini, Alta Frequenza, vol. XLIX, no. 6, Nov. 1980, Milano, Italy, pp. 413–418.
Ktonas et al., Signal Processing, vol. 3, no. 4, Oct. 1980, Amsterdam Netherlands, pp. 373–385.
H. Witte et al., Medical and Biological Engineering and Computing, vol. 29,May 1991, Stevenage, Great Britain, pp. 242–248.
P. H. Boeijinga et al., Electroencephalography and Clinical Neurophysiology, vol. 73, no. 3, Sep. 1989, Ireland, pp. 198–205.
Chen, Y., Laszlo, C. A., and Hershler, C., "A quantitative evaluation of methods for recording surface electromyogram", 15th Annual International Conference of IEEE Engineering in Medicine and Biology Society, San Diego, CA, U.S.A., Oct. 26–31, (1993).
Lindstrom, L. H. and Magnusson, R. I., "Interpretation of myoelectric power spectra: A Model and its applications", Proc. IEEE, 1977, vol. 65, 653–662.
Masuda, T., and Sadoyama, T., "Topographical map of innervation zones within single motor units measured with a grid surface electrode", IEEE T–BME, vol. 35, no. 8, 623–628, Aug. 1988.
McKingley, C. A., and Parker, P. A., "A beamformer for the acquisition of evoked potentials", IEEE Transactions on Biomedical Engineering, vol. 38, no. 4, Apr. 1991, pp. 379–382.

(List continued on next page.)

Primary Examiner—Lee S. Cohen
Attorney, Agent, or Firm—Norman M. Cameron

[57] ABSTRACT

A method and apparatus for monitoring electrical signals propagated through a living organism. A bipolar electrode is placed in contact with the tissue of the organism. Means is operatively connected to the electrode for performing a Hilbert transform on signals from the electrode. The individual electrodes of the bipolar electrode are preferably spaced-apart a distance d so as to satisfy the equation: $|\pi Bd/v| < \pi/2$. The Hilbert transform can be implemented by performing a Fourier transform on the signal, multiplying the signal by the imaginary number j, changing the sign of the signal at all negative frequencies, and then performing a reverse Fourier transform on the signal. The resulting signal is then displayed. Preferably brush tip electrodes are used for EMG signals although the method and apparatus is also applicable to needle electrodes.

15 Claims, 7 Drawing Sheets

OTHER PUBLICATIONS

Reucher, H., Rau, G., and Silny, J., "Spacial Filtering of Noninvasive Multielectrode EMG:Part I–Introduction to measuring technique and application", IEEE T–BME, vol. 34, no. 2, pp. 98–105, Feb. 1987.

Reucher, H., Rau, G., and Silny, J., "Spacial Filtering of Noninvasive Multielectrode EMG:Part II—Filter performence in theory and modeling", IEEE T–BME, vol. 34, no. 2, pp. 106–113, Feb. 1987.

Schwartz, M., Bennett, W. R., and Stein, S., "Communication Systems and Techniques", McGraw–Hill Book Company, New York, 1966, pp. 29–35.

RECORDING BIOLOGICAL SIGNALS USING HILBERT TRANSFORMS

RELATED APPLICATION

This is a continuation-in-part of U.S. patent application Ser. No. 07/969,458 filed Oct. 30, 1992, now U.S. Pat. No. 5,298,572, and of an application filed Nov. 24, 1993 entitled BRUSH-TIP ELECTRODE under Ser. No. 08/156,732, now U.S. Pat. No. 5,443,559.

BACKGROUND OF THE INVENTION

1. Field of the Invention

This invention relates to methods and apparatuses for recording biological signals from living organisms, particularly using bipolar electrodes and Hilbert transforms.

2. Description of Related Art

Nerve and muscle fibers are excitable cells which produce electrical signals propagating along the fibers when excited. The electrical signals propagating along the nerve or muscle fibers are called action potentials (APs). The muscle fibers are organized in groups called motor units (MUs). MUs are the smallest functional groups of muscle fibers innervated by single neurons. When stimulated by a neuron, either all the muscle fibers off a MU will be innervated, or none of them will. The summation of the APs of all the simultaneously activated muscle fibers of a MU is called the MUAP. An electromyographic (EMG) signal is the summation of the repetitive APs of muscle fibers or MUs during muscle contractions. The EMG signals may be used for diagnosis of neuromuscular diseases, investigation of motor control mechanism, and orthotic control. They may be recorded with needle electrodes and, for most superficial muscles, surface electrodes as well. Needle electrodes are inserted into muscle tissue to detect EMG signals, while surface electrodes are placed on the skin above the muscle to detect the signals. Conceptually, surface recording techniques are preferable because they are noninvasive. Nevertheless, needle recording techniques have become the standard and widely used in clinical EMG examinations because surface EMG recording technology had not, prior to this invention, advanced to the point where it could provide as good quality EMG signals as needle recording technology.

Advanced recording technology is required for the use of surface EMG in clinical examinations. What is expected in a surface EMG signal is the detailed information about MUAPs. EMG signals recorded with traditional surface electrodes with large skin-electrode contact area and conventional monopolar or bipolar electrode configurations 10 usually do not contain detailed information about MUAPs. In an effort to develop advanced surface EMG recording methods, a number of avenues have been explored in the literature. Large electrode arrays with more than 50 contacts have been proposed by Masuda and Sadoyamaet [1988] for the investigation of the generation and propagation of the MUAPs. Reucher et al. [1987] suggested pin electrodes with needle points be used as the basic electrodes in an electrode array to reduce the skin-electrode impedance. Reucher et al. also considered spatial filtering techniques which differentiate individual signals obtained with the pin electrodes in the spatial domain to record surface EMG signals selectively. McKingley and Parker [1991] developed a beam former method which improves the signal to noise (S/N) ratio by averaging the signals recorded at different locations along the nerve fibers. In spite of such efforts, no surface EMG recording method has become practical for routine clinical examinations.

In an earlier U.S. patent application. Ser. No. 07/969,458 filed Oct. 30, 1992, Chen et al. describe a practical EMG electrode array. The array is a miniature active electrode array which makes it easy to record multi-channel surface EMG signals. Earlier investigations indicated that the spatial filtering techniques proposed by Reucher et al. are effective in reducing the complexity of the surface EMG signals, but the spatial filters reduce the S/N ratios of the signals significantly.

SUMMARY OF THE INVENTION

It is an object of the present invention to provide a surface EMG recording apparatus and method which are a workable alternative to needle EMG recording technology for routine clinical EMG examinations.

It is another object of the invention to obtain EMG signals on the skin above the muscle with the least distortion to the signal and the least reduction of the S/N ratio.

In accordance with these objects, there is provided an apparatus for monitoring electrical signals propagated through a living organism. The apparatus includes a bipolar electrode and means operatively connected to the electrode for performing a Hilbert transform on a signal frown the electrode.

The bipolar electrode may include a pair of brush tip electrodes. The brush tip electrodes are preferably spaced-apart a maximum distance defined by the equation:

$$|\pi B d/v| < \pi/2$$

Where
 d=distance between the brush tip electrodes, and
 B=frequency band of signals in Hz
 v=average conduction velocity of muscle fibres.

The invention also provides a method for processing electrical signals from an electrode mounted in contact with a living organism. The method includes processing the signals with a Hilbert transform.

The method may include performing a Fourier transform on the signal and multiplying the Fourier transformed signal by $-j\,\mathrm{sgn}(f)$, where $-j$ is the imaginary number and $$\mathrm{sgn}(f) = \begin{cases} 1 & f > 0 \\ 0 & f = 0 \\ -1 & f < 0. \end{cases}$$

DESCRIPTION OF THE PREFERRED EMBODIMENTS

THEORY

Hilbert Transforms

Figure 1:
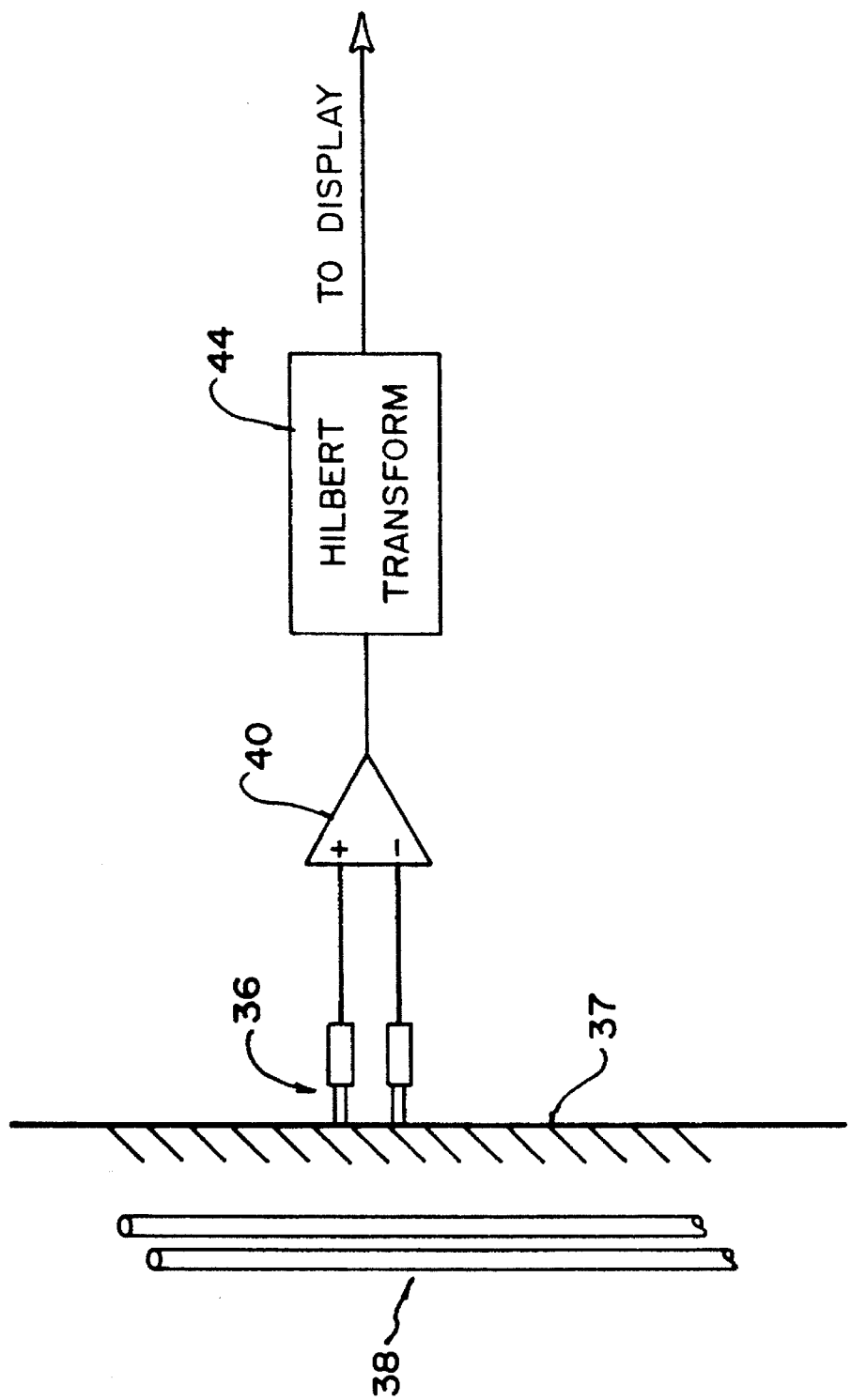
FIG. 1 is a simplified, partly diagrammatic side elevation of an apparatus according to the invention mounted in contact with a living organism.

Hilbert transforms are useful tools in signal analysis and communication theory. The representation of signals by Hilbert transforms makes it easy to describe the modulation and demodulation process in communication theory. However, they are used in this invention not because they are convenient tools for signal analysis, but because they are related to the transfer function of a bipolar electrode. The following are those properties of Hilbert transforms which are relevant for the development of the BEHT method.

The Hilbert transform of a signal x(t) is defined as:

$$x^\tau(t) \equiv H[x(t)] = \frac{1}{\pi} P \int_{-\infty}^{\infty} \frac{x(\tau)}{t-\tau} d\tau \qquad (1)$$

The symbol H[] stands for the "Hilbert transform of", and the character P means to take the principal value of the integral to ensure convergence.

$$H[x^T(t)] = -x(t) \qquad (2)$$

That is, the Hilbert transform of the Hilbert transform of a signal x(t) is the same signal x(t) except for a sign change.

Let the symbol F[] stand for the "Fourier transform of", the following relationship holds:

$$F[H[x(t)]] = -j \, sgn(f) F[x(t)] \qquad (3)$$

where $$sgn(f) = \begin{pmatrix} 1 & f > 0 \\ 0 & f = 0 \\ -1 & f < 0 \end{pmatrix} \qquad (4)$$

Hilbert transforms do not change the amplitude-frequency characteristics of a signal, but they do change the phase-frequency relationship.

The Transfer Function of a Bipolar Electrode

The transfer function of a bipolar electrode has been defined as:

$$F_b(f) = 2j \sin (\pi f d/v) \qquad (5)$$

where d is the interelectrode distance of the bipolar electrode, and v is the conduction velocity of the myoelectric signal to be detected. The bipolar electrode should be placed in the direction of muscle fibers, and the propagation velocity of the myoelectric signal is assumed to be constant.

It has been previously noticed that there are two effects of the bipolar electrode on the myoelectric signal power spectrum: (1) in the low-frequency region, the transfer function behaves like a differentiating filter that adds a positive slope of 6 dB/octave to the spectrum of the signals; (2) at certain frequencies, the transfer function introduces into the spectrum the so-called dips where the amplitude of the spectrum drops to zero. The dips occur at those frequencies where the sine function is equal to zero, i.e., at the following frequencies:

$$f = nv/d \text{ where } n = \pm 1, \pm 2, \ldots \qquad (6)$$

The differentiating property is a desired property because it suppresses some background interference signals which are basically in the low-frequency range, and it improves the selectivity of the electrode. The dips are related to the conduction velocity of the MUAP's and the interelectrode distance of the bipolar electrode, and has been used to estimate the conduction velocity. From the recording point of view, however, the dips are distortion to the "true" myoelectric signal power spectrum because the dips are not the property of the signal, but the property of the electrode. When the interelectrode distanced is small enough that $|\pi B d/v| < \pi$, where B is the frequency bandwidth of the EMG signal, the dips will be out of the frequency range of the signal. From a mathematical point of view this may be restated in the simpler form $|Bd/v| < 1$. However, $\pi$ has been left in above to indicate that both sides of the equation are phases in a sine function ($\pi = 180°$).

It was noticed in the context of the present invention that the sign change of the transfer function across the zero frequency also introduces a distortion to the signal via the nonlinear phase-frequency response. This can be seen more obviously if the transfer function is rewritten under the condition, $$\pi f d/v | < \pi, \text{ as } F_b(f) = 2j \sin (\pi f d/v) = j \, sgn(f) |2 \sin (\pi f d/v)| = |2 \sin (\pi f d/v)| \exp (j\pi/2 sgn(f)) \qquad (7)$$

where | | stands for the "absolute value of" and sgn(f) is defined in equation (4). The phase-frequency response function $\pi/2 \, sgn(f)$ of the bipolar electrode transfer function is nonlinear and hence introduces distortion to the recorded EMG signals.

If the EMG signal on the skin is e(t), referring to the ground, the signal detected by the bipolar electrode is y(t), and the Fourier transforms of the signals are E(f) and Y(f), respectively, then according to equation (7):

Let
$$Y(f) = j \, sgn(f) |2 \sin(\pi f d/v)| E(f) \qquad (8)$$

$$Y'(f) = |2 \sin(\pi f d/v)| E(f) \qquad (9)$$
$$y'(t) = F[Y'(f)] \qquad (10)$$

then, according to equations (3) and (4), one can show that $$y(t) = -H[y'(t)] \qquad (11)$$

So the conclusion was reached that when the interelectrode distance is reduced to avoid the dips in the spectrum of the signal recorded with a bipolar electrode, the transfer function of the bipolar electrode can be expressed as a filter function characterized by the absolute value of the sine function and a Hilbert transform operation plus a sign change.

The Bipolar Electrode-Hilbert Transform Recording Method

The transfer function of a bipolar electrode introduces phase distortion to the EMG signal in spite of its filtering function characterized by a sine function when the interelectrode distance d satisfies $|\pi B d/v| < \pi$. The phase distortion can be expressed as a Hilbert transform operation. According to equation (2), the Hilbert transform of the Hilbert transform of a signal is the same signal except a sign change.

Thus, the phase distortion can be corrected by applying a Hilbert transform to the EMG signal recorded with a bipolar electrode with an interelectrode distance d which satisfies $|\pi Bd/V|<\pi$. From equation (8) to (11), the phase-corrected signal will be where
$$H[y(t)] = H[-H[y'(t)]] = y'(t) = F[Y'(f)] \quad (12)$$
$$Y'(f) = |2 \sin (\pi fd/v)|E(f)$$
$$E(f) = F[e(t)]$$
$$|\pi Bd/v| < \pi$$

and e(t) is the EMG signal when measured with a monopolar electrode.

The condition, $|\pi Bd/v|<\pi$, is to ensure that the dips in the transfer function of the bipolar electrode do not fall within the frequency range of the EMG signal. Since the bipolar electrode is used to introduce high-pass filtering effect to compensate the low-pass filtering effect of the volume conduction, it is required that the negative slope after the turning point of the sine function should also be kept out of the frequency band of the EMG signal. This means that the interelectrode distance d of the bipolar electrode should also satisfy the following condition:

$$|\pi Bd/v|<\pi/2 \quad (13)$$

Therefore, the maximum allowed interelectrode distance $d_{max}$ can be calculated from $|\pi Bd_{max}/v|=\pi/2$. For example, suppose the average conduction velocity v of muscle fibers is 3.2 mm/msec, the frequency band B of surface EMG signals is within 500 Hz. Then, the maximum interelectrode distance $d_{max}$ turns out to be $d_{max}=3.2$ mm. When the interelectrode distance d is smaller than the maximum distance $d_{max}$, is guaranteed that the dips will not present in the spectrum of the recorded signals, and the bipolar electrode will always boost the high frequency components and suppress the low frequency components in the signal. For larger muscles which may have higher muscle conduction velocity of, say 5 mm/msec, the interelectrode distance may be larger up to 5 mm. Choosing smaller interelectrode distance is safe to satisfy the conditions listed above, but smaller interelectrode distance means larger reduction of the signal amplitude. An interelectrode distance of 2.5 to 4 mm is preferred depending the size of the muscle to be measured.

Figure 2:
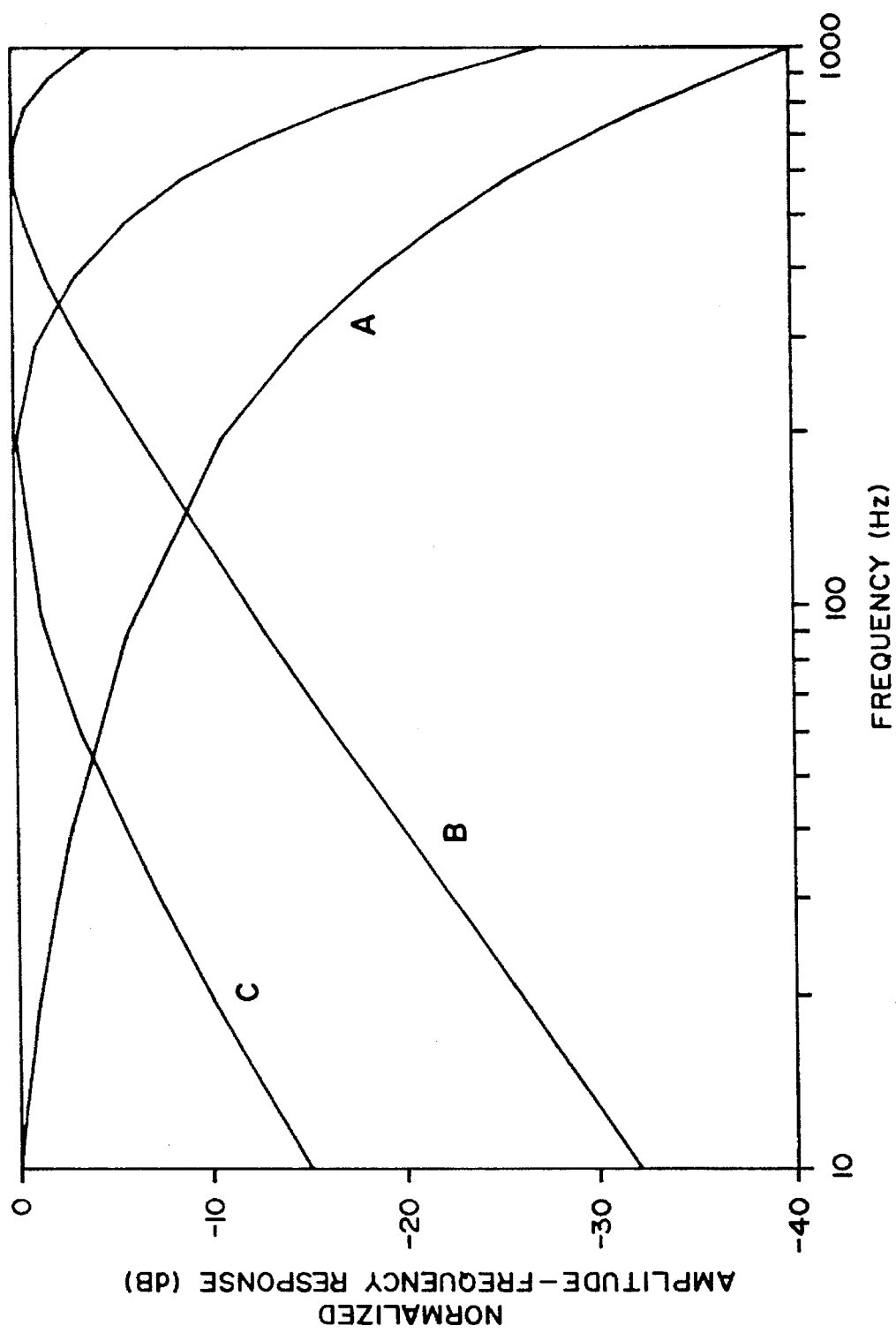
FIG. 2 is a graph showing filter functions in EMG recordings with surface bipolar electrodes.

When the interelectrode distance of the bipolar electrode is chosen to satisfy $|\pi Bd/v|<\pi/2$, the BEHT recording unit will boost the high frequency components and suppress the low frequency components of the surface EMG signal, and compensates very effectively for the signal components at high frequencies attenuated by volume conduction. As a result, EMG signals obtained with BEHT recording units reflect the underlying myoelectric activities truthfully. In fact, it was shown previously that the filter function of the volume conduction is as follows:

$$F_{vc}(f)=K_0(2\pi fh/v)K_0(2\pi fa/v) \quad (14)$$

where $K_0(x)$ is the modified Bessel function of the second kind, order 0, h denotes the radial distance from the fibre to the point of measurement, a is the fibre radius, and v is the conduction velocity of the fibre. For simplicity, only a single fibre is considered here. Suppose the myoelectric signal at the source site (close to the fibre) be e'(t), and $E'(f)=F[e'(t)]$, then, $$E(f)=F_{vc}(f)E'(f) \quad (15)$$

therefore, $$Y'(f)=|2 \sin (\pi fd/v)|F_{vc}(f)E'(f)=E'(f) \quad (16)$$

where $F_{vcb}(f)$ denotes the combined filter function for both the BEHT recording unit and the volume conduction. What is desired is to have $F_{vcb}(f)$ as flat as possible in the interested frequency range, and the attenuation caused by $F_{vcb}(f)$ as small as possible. The former requirement ensures that the least distortion to the signal is introduced, and the latter ensures that best S/N ratio is obtained. FIG. 2 shows an example which illustrates how the filter function of a BEHT recording unit compensates the filter function of the volume conduction to form a flatter combined filter function in the interested frequency range of 50–500 Hz. In the example, the fibre radius is assumed to be 40 μm, the conduction velocity to be 3.2 m/sec., the interelectrode distance to be 2.5 mm, and the distance between the fibre and the electrode to be 2 mm. All the amplitude-frequency responses have been normalized for easier comparison. It can be seen that 1) the volume conduction behaves like a low-pass filter, 2) the BEHT recording unit has a high-pass filtering effect, and 3) the combined filter function, $F_{vcb}(f)$, is relatively flat in the frequency range 50–500 Hz. The wider frequency band of the combined filter function implies that the EMG signals recorded with the BEHT recording unit will suffer less distortion caused by both the volume conduction and the recording system, and will have better resolution in terms of the MUAPs in the signals.

Figure 3:
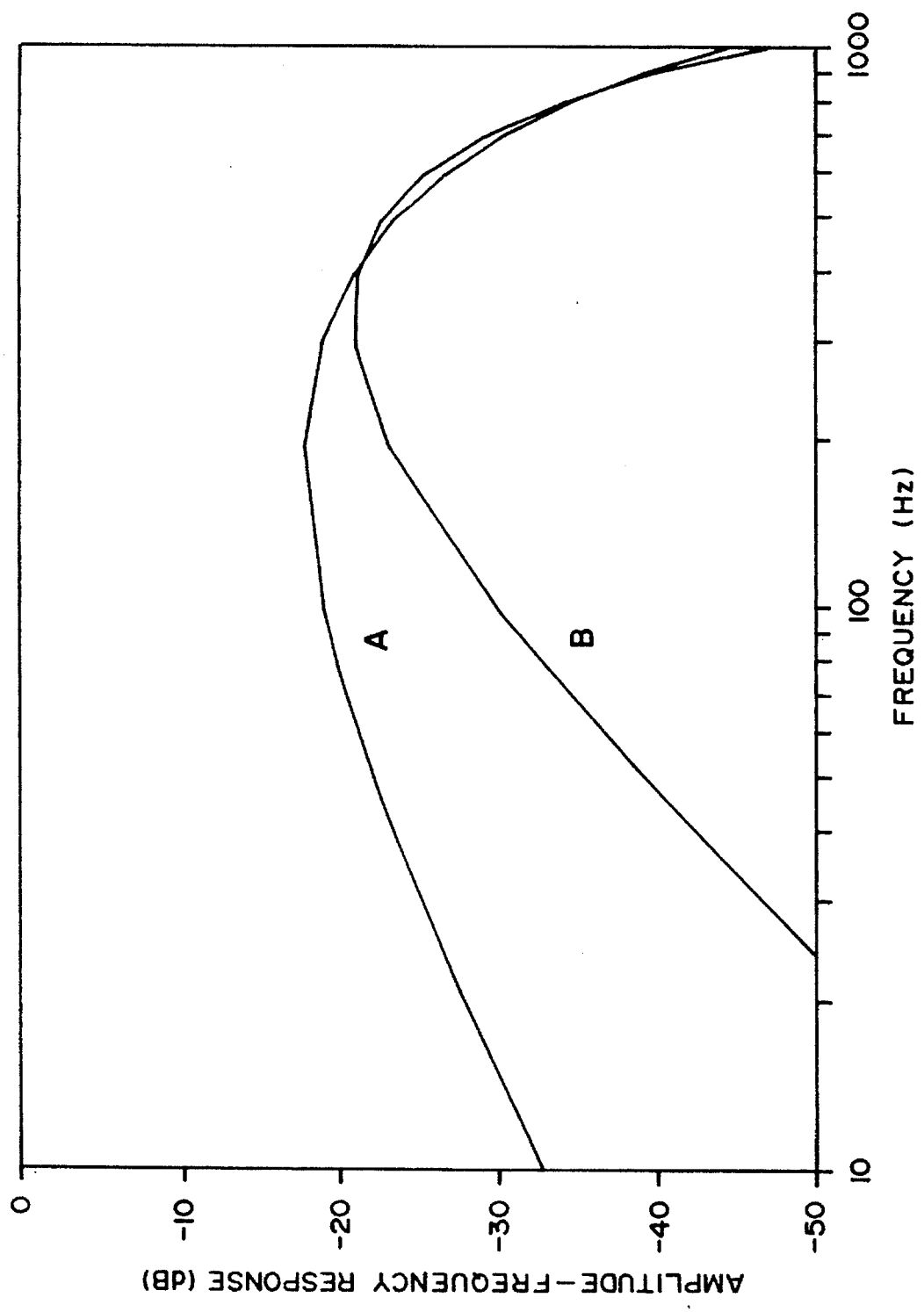
FIG. 3 is a graph showing combined filter functions for volume conduction and recording methods.

It has been shown that the double differentiating spatial filtering (DDSF) is the best choice among the spatial filtering methods. Compared to the DDSF method, the BEHT method is an even better choice. This is because EMG signals recorded with the BEHT method suffer less distortion, and have higher S/N ratios. FIG. 3 shows typical combined volume conduction—electrode filter functions for both the DDSF and BEHT recording methods. Again, the muscle fibre radius is assumed to be 40 μm, the conduction velocity to be 3.2 m/sec., the interelectrode distance to be 2.5 mm, and the distance between the fibre and the electrode to be 2 mm. It can be seen that a flatter frequency response in the interested frequency band is obtained with the BEHT method, which implies that the recorded signal will be less distorted when BEHT method is used. It can be also seen that the combined filter function for the BEHT method covers a larger area in the interested frequency band, which implies that the recorded signal will contain larger energy. Hence EMG signals recorded with the BEHT method will have higher S/N ratios.

Figure 4:
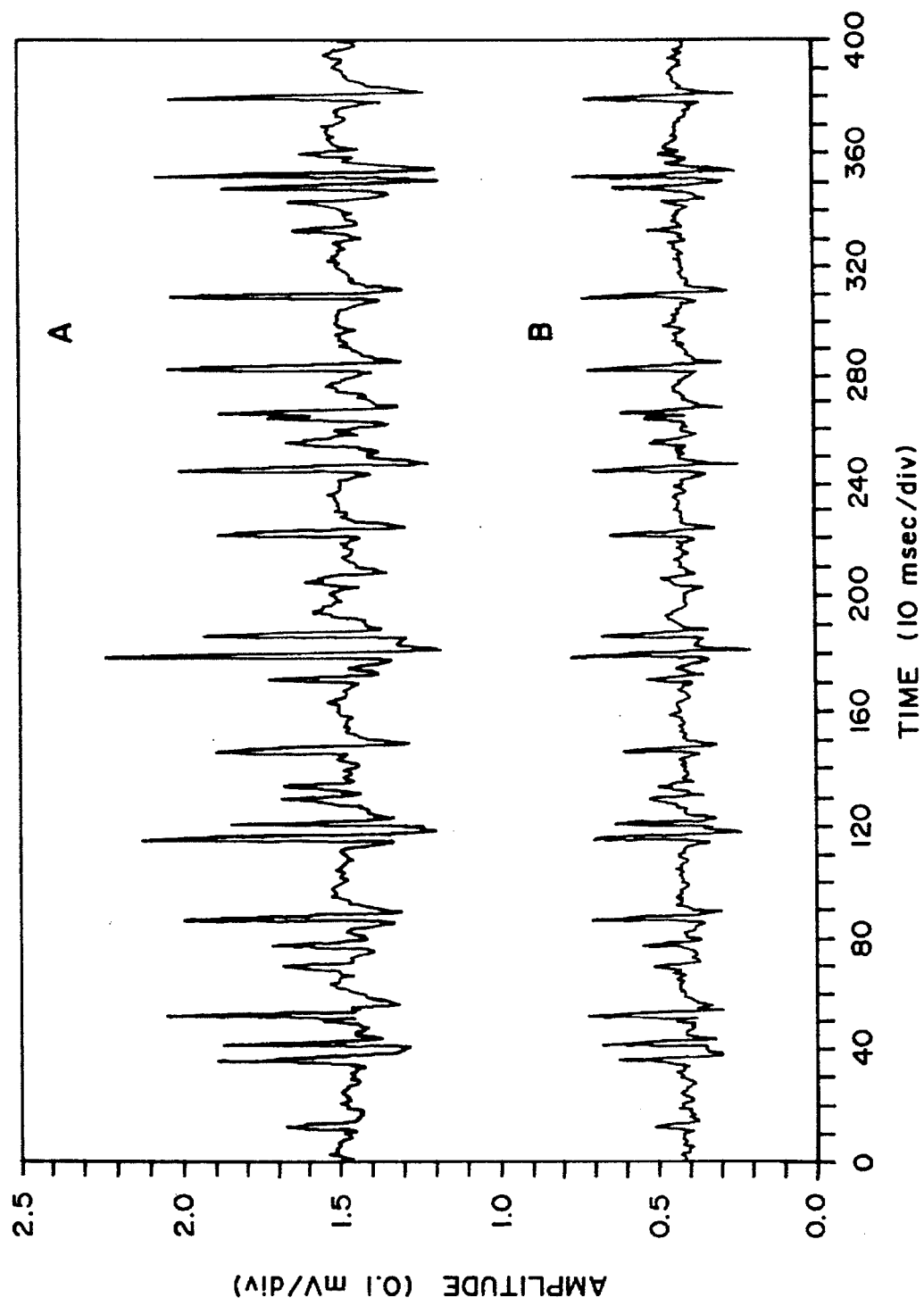
FIG. 4 is a graph comparing BEHT and DDSF recording methods.

FIG. 4 shows two typical traces of EMG signals recorded with the DDSF and BEHT methods, respectively. The two signals were recorded simultaneously at the same location on the skin above the abductor pollcies brevis (APB) muscle during weak voluntary contraction. A brush-tip electrode array with an interelectrode distance of 2.5 mm was used. The spikes with single peaks in the signals are typical MUAPs. It is obvious that MUAPs detected with the BEHT method have higher amplitude than those detected with the DDSF method. However, the distortion to the signals caused by the volume conduction and recording methods is hard to evaluate for the two EMG signals since no reference is available for such evaluation.

APPARATUS

Figure 8:
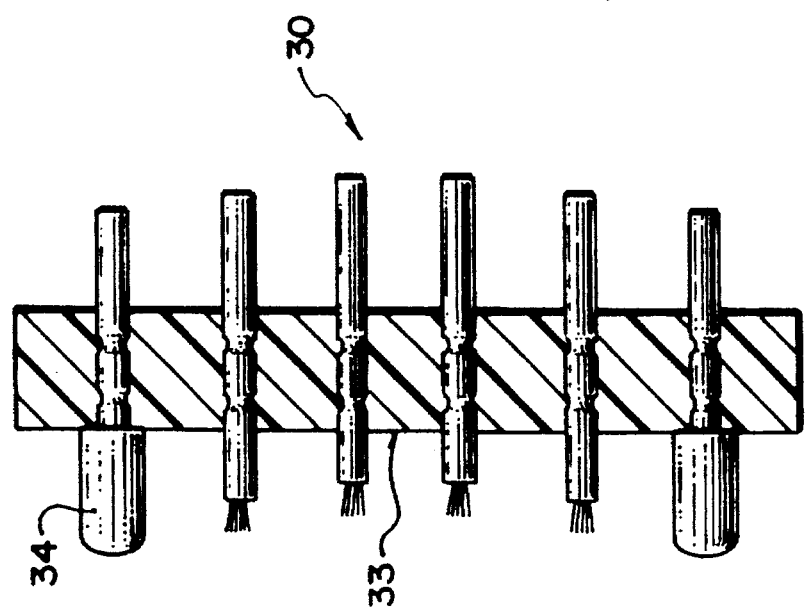
FIG. 8 is a sectional view taken along line 8—8 of FIG. 7.
Figure 7:
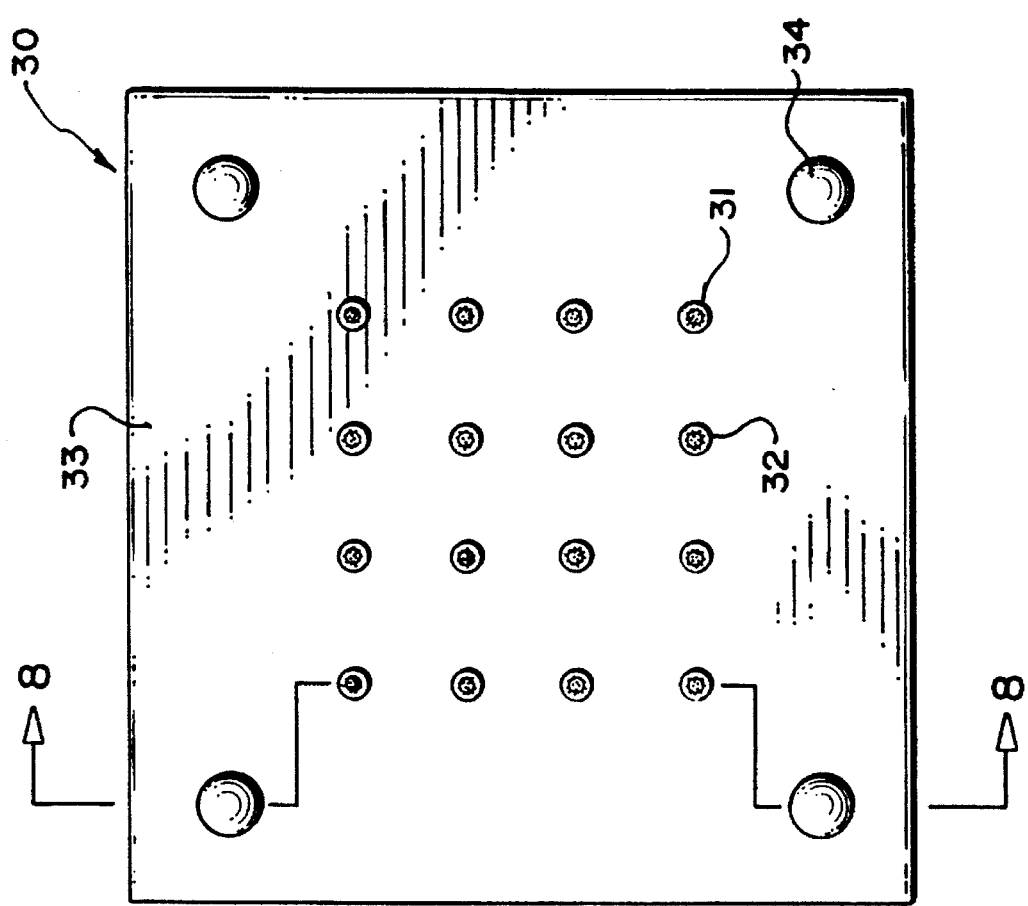
FIG. 7 is a bottom plan view of a brush-tip electrode array.

A bipolar electrode is defined as an electrode with two contacts for detecting the same potentials at slightly different locations. The characteristics of the electrode consists of 1) the mechanism for detecting the potentials on the contact interface; 2) the size of the individual contacts; 3) the distance between the two contacts. For surface electrodes, the individual contacts can be made independently. Such individually made contacts are called basic electrodes. A brush-tip electrode is an example of a basic electrode. Two adjacent brush-tip electrodes in an electrode array are used to form a bipolar electrode in this example. Referring to FIG. 7 and 8, array 30 includes 16 brush-tip electrodes, including electrodes 31 and 32, which are spaced-apart 2.54 mm in this instance. Pairs of these electrodes, such as electrodes 31 and 32, form the bipolar electrodes. In this instance the electrodes are mounted on an insulating mount 33. There are also larger electrodes 34 which support the brush-tip electrodes, preventing possible high pressure between the skin and these electrodes when the array is applied to the skin surface.

Figure 6:
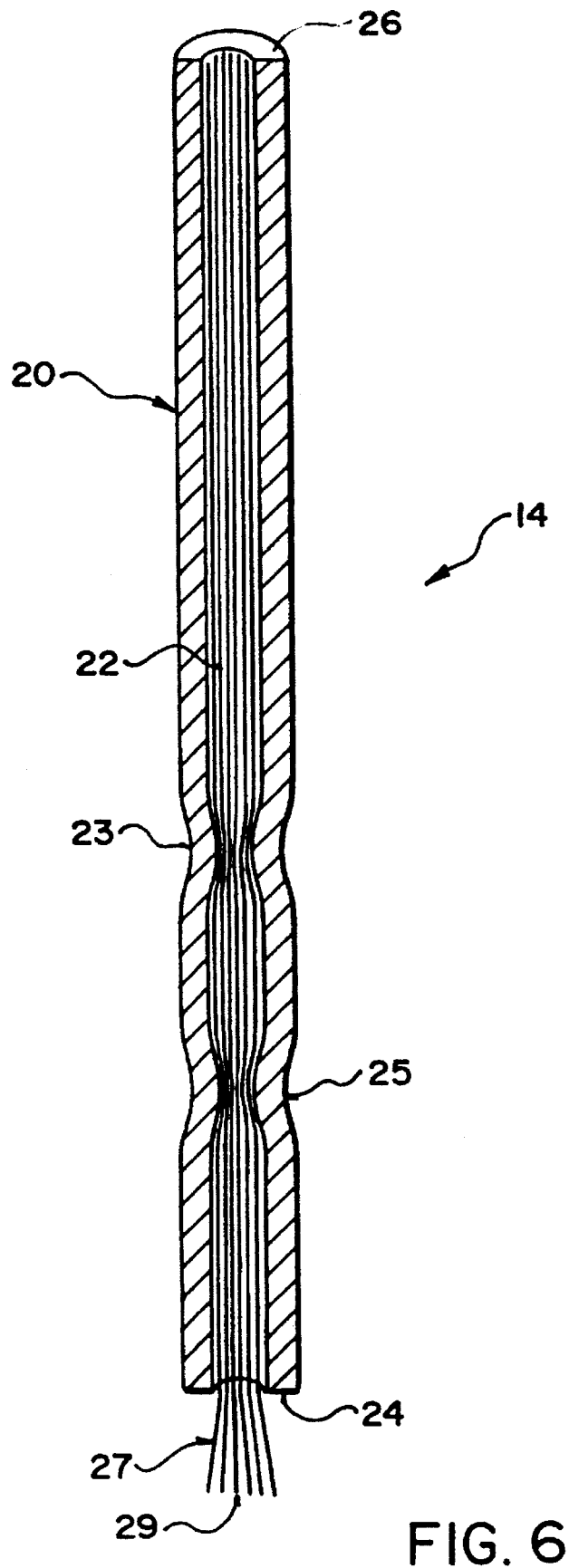
FIG. 6 is a side elevation, partly in section, a brush tip electrode according to an embodiment of the invention.

Referring to FIG. 6, this shows a brush tip electrode 14 of the type employed which includes a tube 20 about 0.5 mm in diameter in this example. A medical injection needle cut to a length of 10 mm was used. The tube produced has an inside diameter of 0.25 mm. Other hard elastic metal tubes could be substituted. A plurality of thin but hard and resilient wires 22 extend through the tube and outwardly from its bottom 24. There should be at least 10 wires, preferably 20–50. Thirty tungsten wires were used in this example, tungsten being preferred for its hardness and corrosion resistance in the presence of salt. High hardness stainless steel is a less expensive alternative. Each wire should have a diameter less than 100 µm, preferably 20–80 µm. In this example the diameter is about 30 µm. Thus the bunch of wires has a diameter of 0.25 mm in this example which is equal to the inside diameter of the tube. The diameter of the electrode should in any case be less than 2.54 mm, preferably less than 1 mm.

The fine wires are held firmly by crimping the tube at locations 23 and 25 which are about 2 mm apart. The wires are cut even with top end 26 of the tube and project 0.5–2.5 mm from the bottom 24 of the tube, preferably 0.7–1.7 mm and most preferably 1.0 mm as in this example. The wires are slightly splayed below the bottom of the tube, forming a tiny brush tip 27 and leaving room for individual wires to be bent a bit within the elastic deformation range of the wires. This allows the lengths of the wires to adjust to fit a skin surface which is rough from a microscopic point of view. The approximate area of end 29 of the brush tip is 0.05–0.07 mm$^2$. In this example the area is 0.049$^2$ mm with a diameter of 0.25 min. The end 29 is seen to be formed by the ends of the individual wires 22 and is therefore rough, multi-pointed and abrasive.

A pair of the brush tip electrodes 14 are used to form the bipolar electrode 36 shown in FIG. 1. As discussed, these electrodes are preferably spaced 2.5–4 mm apart. A maximum distance of 3.2 mm is acceptable for most muscles although up to 5 mm may be suitable for larger muscles. The electrodes are shown in contact with the skin 37 of a patient so as to receive EMG signals from the muscle or nerve fibers 38. It should be understood however that the bipolar electrode does not have to be made with brush-tip electrodes, provided the interelectrode distance satisfies equation 13. For example, the BEHT method can be used in the detection of motor/sensory nerve action potentials (APs). In such cases the individual electrode diameter and interelectrode distance can be 10 times larger than for muscle fibers because nerve fibers have a conduction velocity about 10 times larger than muscle fibers.

Figure 5:
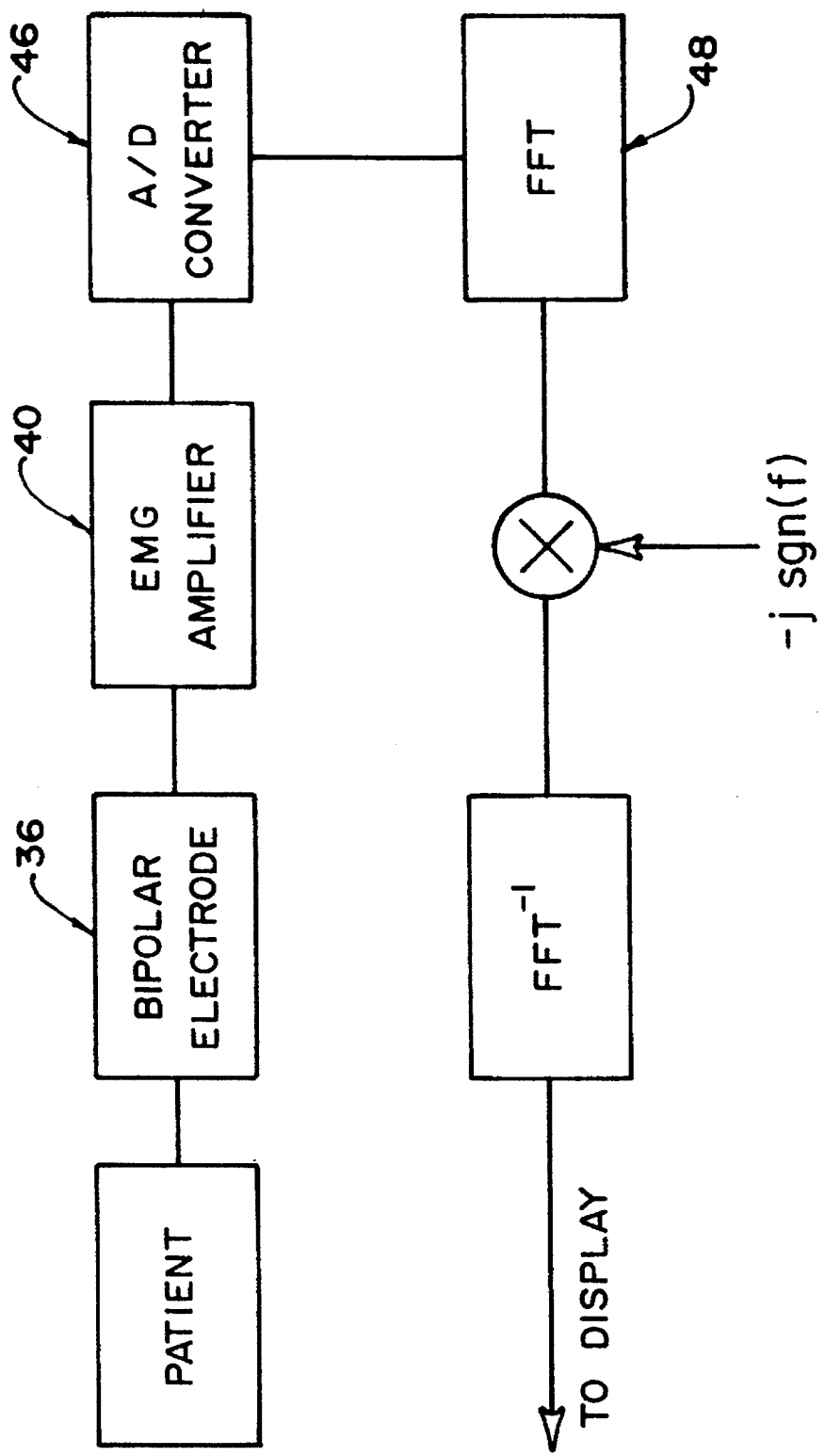
FIG. 5 is a flow chart of a BEHT recording method according to the invention.

The bipolar electrode is connected to a differential amplifier 40 to form a bipolar electrode configuration. The EMG signal is amplified by the amplifier which is connected to the Hilbert transform equipment shown generally at 44 in FIG. 1. Referring to FIG. 5, the Hilbert transform is accomplished firstly by an analog/digital (A/D) converter 46 which converts the analog signal from the amplifier into a digital signal. The A/D converter is connected to means 48 for performing a Fast Fourier Transform (FFT) of the signal. This can be accomplished by hardware or software. For real-time display of the EMG signal, it is preferable to use a specialized digital signal processing (DSP) board to perform the FFT operation. For short EMG signals, however, a well written FFT program in C language is sufficient to perform the transforms on line in a personal computer based EMG machine.

Many suitable FFT programs are available in a variety of books. The FFT programs used in the implementation of the EMG recording method in this example were from Chapter 12 (pp. 398–470) of *Numerical Recipes in C-The Art of Scientific Computing* (by William H. Press, Brian P. Flannery, Saul A. Teukolsky, and William T. Vetterling, Cambridge University Press 1988, except for computer programs and procedures, which are from Numerical Recipes Software 1987, 1988). The recording method was not implemented with a DSP board in this example since the EMG signal recorded was one second long, and software implementation was fast enough. If faster FFTs are needed for recording long signals, a DSP board is a better choice because most commercially available DSP boards can be used to perform FFT in a much faster speed than a program executed in a personal computer.

The Fourier transformed EMG signal is then multiplied by the imaginary number, −j, and the sign of the signal at all negative frequencies is changed. The multiplication of two imaginary or complex, numbers together is an operation well known in electrical engineering and involves the summation and multiplication of four real numbers. Finally, the modified signal in frequency domain is converted back to time domain with the inverse Fast Fourier Transform (FFT$^{-1}$). The resultant is the EMG signal to be recorded. The FFT$^{-1}$ operation is performed in a similar manner to the FFT operation using either hardware or software.

Although the BEHT method was developed primarily for recording surface EMG signals, there is no reason why it could not be used for recording needle EMG signals and motor and sensory nerve action potentials. When needle EMG signals are to be recorded, a bipolar needle electrode should be used. Also, the bipolar needle electrode should be inserted into the muscle and maintained in a position that the two contacts of the electrode are located along the muscle fibers. For recording nerve APs, surface bipolar electrodes may be used. Since the conduction velocity of nerve fibers is higher than that of muscle fibers, the interelectrode distance of the bipolar electrode can be larger. As a consequence, the size of contacts of the bipolar electrodes for recording nerve APs can be larger than that of the electrodes for the EMG signals.

It will be understood by someone skilled in the art that many of the details provided above are by way of example only and can be modified or deleted without departing from the scope of the invention which is to be interpreted with reference to the following claims.

What is claimed is:

1. An apparatus for monitoring electrical signals propagating through a living organism, the apparatus comprising:

a bipolar electrode; and means operatively connected to the electrode for performing a Hilbert transform on a signal from the electrode.

2. An apparatus as claimed in claim 1, further including a differential amplifier operatively connected between the bipolar electrode and said means.

3. An apparatus as claimed in claim 2, wherein the means for performing a Hilbert transform includes means for performing a Fourier transform on the signal.

4. An apparatus as claimed in claim 3, further including means for multiplying the Fourier transformed signal by:

$$-j\ \text{sgn}(f)$$

where j is an imaginary number and $$\text{sgn}(f) = \begin{cases} 1 & f > 0 \\ 0 & f = 0 \\ -1 & f < 0. \end{cases}$$

5. An apparatus as claimed in claim 4, further including means for performing an inverse Fourier transform on the signal multiplied by −j sgn(f).

6. An apparatus as claimed in claim 5, wherein the apparatus includes an analog/digital converter operatively connected between the amplifier and the means for performing a Fourier transform.

7. An apparatus as claimed in claim 6, wherein the means for performing a Fourier transform and the means for performing an inverse Fourier transform include a digital signal processor.

8. An apparatus as claimed in claim 1, wherein the bipolar electrode includes a pair of spaced-apart brush tip electrodes.

9. An apparatus as claimed in claim 1, wherein the bipolar electrode includes a pair of individual electrodes which are spaced-apart a maximum distance defined by:

$$|\pi B d/v| < \pi/2$$

where d = distance between the electrodes
B = frequency band of signals in Hz; and
v = average conduction velocity of tissue of organism.

10. An apparatus as claimed in 9, wherein the individual electrodes are spaced-apart 2.5–4 mm.

11. An apparatus as claimed in claim 9, wherein the individual electrodes are spaced-apart a maximum distance of 3.2 mm.

12. A method of evaluating biological signals from a living organism, comprising:

applying a bipolar electrode to tissue of the organism;

processing signals from the electrode using Hilbert transforms; and recording the processed signals.

13. A method as claimed in claim 12, wherein the bipolar electrode comprises a pair of spaced-apart individual electrodes which are spaced-apart on the living organism a distance d so as to satisfy the condition:

$$|\pi B d/v| < \pi/2.$$

14. A method as claimed in claim 12, including the steps of first converting the signals to digital form and performing the Hilbert transforms with a digital processor.

15. A method as claimed in claim 14, wherein the processor implements the Hilbert transforms by first generating a Fourier transform of the signals, then multiplying the Fourier transformed signals by:

$$-j\ \text{sgn}(f)$$

where j is the imaginary number and $$\text{sgn}(f) = \begin{cases} 1 & f > 0 \\ 0 & f = 0 \\ -1 & f < 0 \end{cases}$$

and generating an inverse Fourier transform of the signals so multiplied.

* * * * *